United States Patent [19]

Lathrop

[11] Patent Number: 5,607,461
[45] Date of Patent: Mar. 4, 1997

[54] APPARATUS AND METHOD FOR DELIVERING ELECTRICAL STIMULUS TO TISSUE

[75] Inventor: Peter H. Lathrop, San Diego, Calif.

[73] Assignee: NexMed, Inc., Los Angeles, Calif.

[21] Appl. No.: 545,945

[22] Filed: Oct. 20, 1995

[51] Int. Cl.$^6$ ..................................... A61N 1/20
[52] U.S. Cl. ................... 607/75; 607/50; 607/2; 607/145; 607/115; 128/639
[58] Field of Search ................. 607/1, 3, 2, 45, 607/46, 48, 50, 52, 58, 75, 115, 118, 134, 135, 142, 145–149, 98, 99, 150; D24/187, 200, 144, 170; 128/639, 644

[56] References Cited

U.S. PATENT DOCUMENTS

| | | | |
|---|---|---|---|
| 4,112,923 | 9/1978 | Tomecek | 607/1 |
| 4,770,328 | 9/1988 | Dickhudt et al. | 607/2 |
| 4,803,986 | 2/1989 | Dufresne et al. | 607/115 |
| 4,917,092 | 4/1990 | Todd et al. | 607/46 |
| 4,934,367 | 6/1990 | Daglow et al. | 607/37 |
| 5,133,352 | 7/1992 | Lathrop et al. | 607/50 |
| 5,254,081 | 10/1993 | Maurer et al. | 607/149 |

*Primary Examiner*—William E. Kamm
*Assistant Examiner*—George R. Evanisko
*Attorney, Agent, or Firm*—J. Winslow Young

[57] ABSTRACT

An electrical stimulation apparatus and method for applying an electrical stimulation to a lesion. The apparatus includes a housing having a battery and an electrical circuit mounted inside the housing. A pair of electrodes are removably mounted to the housing and extend therefrom so as to accommodate being touched to the skin on opposite sides of the lesion. A switch on the housing allows the user to selectively supply electrical energy to the electrodes. A first light on the housing is illuminated when the switch is depressed thereby providing a visual indication that electrical energy is being supplied to the electrodes. A second light on the housing provides a visual indication of a low battery condition. A closure is mountable to the housing and encloses the electrodes, switch, and light within the closure. The size and shape of the housing and closure are specifically designed to allow the user to carry the electrical stimulation apparatus at all times and to encourage its frequent use at any time and under almost any circumstance.

15 Claims, 2 Drawing Sheets

APPARATUS AND METHOD FOR DELIVERING ELECTRICAL STIMULUS TO TISSUE

BACKGROUND

1. Field of the Invention

This invention relates to the electrical stimulation of living tissue and, more particularly, to a convenient, portable electrical stimulation apparatus and method for selectively delivering electrical stimulation to living tissue.

2. The Prior Art

The beneficial results from electrical stimulation of living tissue are well known in the art and range from devices for the combined nerve fiber and body stimulation such as shown in U.S. Pat. No. 5,117,826 to the method for treating herpes simplex as shown in U.S. Pat. No. 5,133,352. Other devices within this general category include the small size, low frequency curing apparatus shown in U.S. Pat. No. 4,922,906; the electrotherapeutic treatment apparatus shown in U.S. Pat. No. 5,107,835; the method for the treatment of herpes simplex and herpes zoster shown in U.S. Pat. No. 4,913,148; and the low frequency electrotherapeutic device shown in U.S. Pat. No. 5,133,351, to name a few.

An examination of each of these known references reveals a rather complex device which involves extensive preparation for use or is otherwise too cumbersome to be readily portable. However, I have found that the development of a herpes-caused lesion is preceded by an associated nerve sensation that signals to the patient that such a lesion is in the developmental stage. I have also found that timing is critical in the application of the electrical stimulus to the lesion site. Specifically, it is important that the patient have the ability to promptly apply electrical stimulation to the potential lesion site especially before the lesion appears with the site selection being based solely upon the pre-lesion nerve sensation. This, in turn, requires that the electrical stimulation apparatus should be readily accessible in a convenient, hand-portable configuration to thereby provide the user with the capability to promptly and even discretely apply electrical stimulation to any predetermined site on the body. Such an apparatus and method is disclosed and claimed herein.

BRIEF SUMMARY AND OBJECTS OF THE INVENTION

This invention involves a novel electrical stimulation apparatus and method for delivering electrical stimulation to a preselected area of the skin. The apparatus is a small, hand-held housing containing a battery, an electrical circuit, a switch, and a pair of electrodes removably mounted to the device. A two color light system provides a visual indication to show that the device is operational or if there is a low-battery condition. A closure telescopically engages the housing to encase both the electrodes and the switch and to present a smooth profile to the apparatus. The apparatus is small enough that it conveniently fits within the hand of the user and is mountable on a key chain. The small size, convenience of use, and pleasing visual appearance all lend themselves to rendering the apparatus easy to carry and simple use to further encourage its frequent use by persons who would benefit from the application of electrical stimulus with my novel apparatus and method. The electrodes are releasably mounted to the device for ease of replacement.

It is, therefore, a primary object of this invention to provide improvements in apparatus for delivering electrical stimulation to living tissue.

Another object of this invention is to provide improvements in the method of delivering electrical stimulation to living tissue.

Another object of this invention is to provide a small, hand-portable electrical stimulation apparatus.

Another object of this invention is to provide a smooth-contoured, relatively small electrical stimulation apparatus.

Another object of this invention is to provide an electrical stimulation apparatus having a pair of removable electrodes.

Another object of this invention is to provide an electrical stimulation apparatus having a closure for enclosing the electrodes and the switch.

Another object of this invention is to provide a light system for visually indicating that the device is operational.

Another object of this invention is to provide an indicator system to indicate when there is a low battery condition.

These and other objects and features of the present invention will become more readily apparent from the following description and the appended claims.

DETAILED DESCRIPTION OF THE PREFERRED EMBODIMENT

Figure 1:
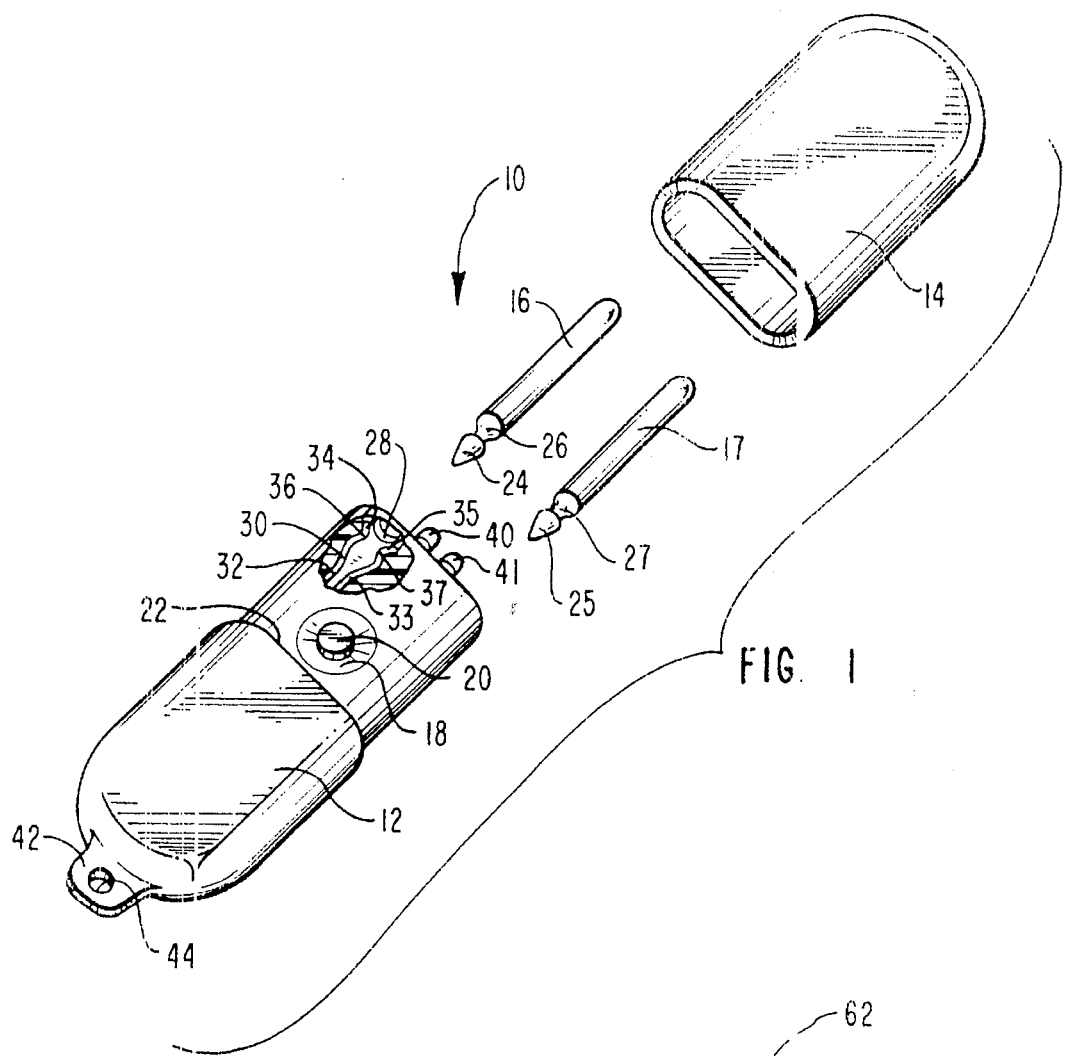
FIG. 1 is an exploded, perspective view of a presently preferred embodiment of my novel electrical stimulation apparatus and its closure.

The invention is best understood by reference to the drawing wherein like parts are designated by like numerals throughout in conjunction with the following description.

General Discussion

I have invented a novel, hand-portable electrical stimulation apparatus and method for enabling the user to selectively apply electrical stimulation to the skin at preselected locations and at any predetermined time or time interval. This novel feature is made possible by reason of the relatively small size and convenience with which my novel electrical stimulation apparatus can be used. Further, I have specifically designed my novel device with a smooth, aesthetically pleasing external profile so as to render it more amenable to being carried continually by the user. To facilitate its being carried at all times by the user I have also included an attachment site for making it possible to releasably attach the electrical stimulation apparatus to a key chain or the like.

My electrical stimulation apparatus is configured as a housing and a closure that releasably fits on the end of the housing. The housing contains the battery and the electronic circuitry as well as an externally accessible switch. A pair of electrodes are releasably attached to the housing and are adapted to being touched to the skin to provide the electrical contact with the skin. The electrodes are releasably attached to the housing in order to allow them to be readily sterilized or replaced in the event replacement is required for medical reasons. The housing is configured with a relatively small external profile so as to allow it to be easily held in and, possibly, even concealed within the confines of the user's hand. This feature contributes to the overall effectiveness of my electrical stimulation apparatus in that it allows the user to discretely apply electrical stimulation where one would otherwise be intimidated into not using this novel invention. For example, if a user were attending a concert and felt the early stages of a herpes lesion on the lip, the user will be able to discretely palm my electrical stimulator and touch the electrodes to the affected area on the lip and the thereby effectively inhibit the formation of a lesion thereon.

The switch is mounted on the housing at a location where it is concealed by the closure when the closure is mounted to the housing. This configuration precludes inadvertent activation of the switch when the electrical stimulation apparatus is not in use and is being carried in a pocket, purse, or the like.

A light system is mounted on the housing at a position generally between the electrodes and provides the user with a visual indication when adequate electrical energy is being supplied to the electrodes upon activation of the switch. This is an important feature since the electrical energy supplied to the electrodes by the electrical stimulation apparatus is of such a low power as to be tactilely undetectable by the user. The light thereby assures the user that sufficient electrical energy is being delivered to the electrodes. The second light visually indicates to the user that the battery is in a low-battery condition and is failing to deliver sufficient electrical energy to supply the electrical stimulation of this invention. In this instance, one light may be red for a low battery condition, while the other light may be green when the switch is closed to indicate that the device is functioning properly.

DETAILED DESCRIPTION

Figure 2:
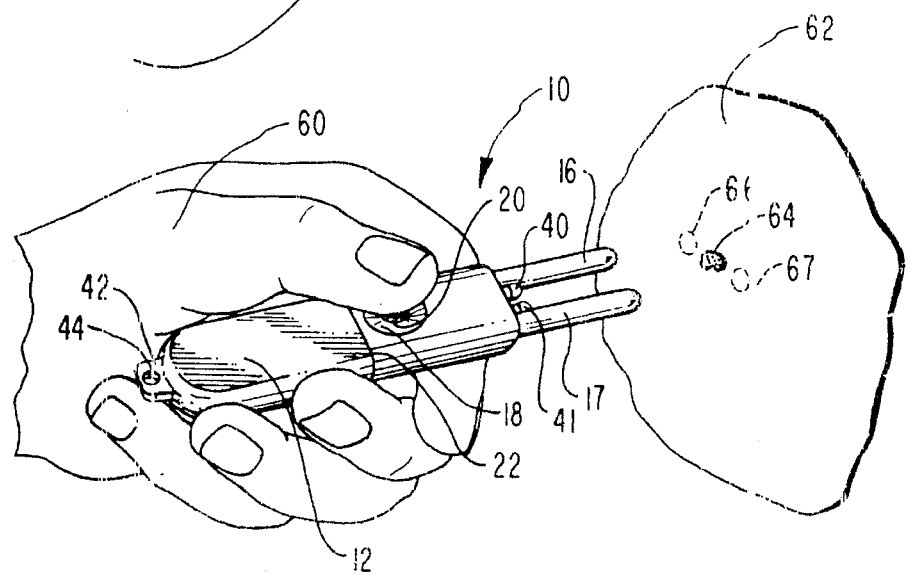
FIG. 2 is a perspective view of the electrical stimulation apparatus of FIG. 1 shown in the environment of a hand and an area of skin.

Referring now to FIGS. 1 and 2, the novel electrical stimulation apparatus of my invention is shown generally at 10 and includes a housing 12, a closure 14, and a pair of replaceable electrodes 16 and 17 removably mounted to housing 12. An activation switch 20 is nested within a recess 18 on one side of housing 12 and is adapted to be concealed beneath closure 14 when closure 14 is secured to housing 12. Housing 12 includes an undercut section 22 around the vicinity of switch 20 so as to accommodate closure 14 telescopically receiving electrodes 16 and 17 along with switch 20 to thereby enclose all of these elements within the confines of closure 14. Undercut section 22 and closure 14 are both dimensionally configured so that closure 14 is snugly engageable to housing 12 in a snap-fit relationship. Exteriorly, closure 14 cooperates with housing 12 to provide a continuous, smooth external profile to all of electrical stimulator apparatus 10 as represented by the external surfaces of housing 12 and closure 14. A retainer 42 is formed on the end of housing 12 and includes a hole 44 therethrough for the purpose of attaching electrical stimulator apparatus to a key chain, identity tag, or the like.

Housing 12 is configured to releasably engage each of electrodes 16 and 17 in a snap-fit relationship. Specifically, with reference to electrode 16, a cutaway section is shown in housing 12 in order to reveal the snap-fit relationship between housing 12 and electrode 16. Electrode 16 is configured with a pointed end 24 having a circumferential groove 26 around the base of pointed end 24. A hole 28 is formed in housing 12 to enable pointed end 24 to be inserted therethrough into engagement with spring clip 30. Spring clip 30 is formed from a pair of resilient, metal strips 32 and 33 each of which are mirror images of the other and respectively include sloped surfaces 34 and 35 which terminate in inwardly directed detents 36 and 37. Sloped surfaces 34 and 35 receive pointed end 24 which forces apart metal strips 32 and 33 until groove 26 is engaged by detents 36 and 37. The resiliency of metal strips 32 and 33 provides spring clip 30 with the necessary retention force to releasably hold electrode 16 in housing 12. Removal of electrode 16 is readily accomplished by the user (not shown) firmly grasping electrode 16 and sharply pulling electrode 16 outwardly to cause detents 36 and 37 to disengage from groove 26. Electrode 16 may then be sterilized or even discarded and replaced with another electrode 16.

Housing 12 includes lights 40 and 41 mounted to the end thereof at a position between electrodes 16 and 17. Light 40 provides a visual indicator to the user (not shown) when switch 20 is activated and that adequate electrical energy is available for electrodes 16 and 17. The presence of light 40 is particularly important in that the electrical current supplied to electrodes 16 and 17 is of such a low magnitude as to be undetectable when electrical stimulator apparatus 10 is applied to tissue. On the other hand, light 41 provides a visual indication to the user that a low battery condition exists in electrical stimulator apparatus 10 such that insufficient electrical energy is available to electrodes 16 and 17. Either light 40 or light 41 will become illuminated upon closure of switch 20 thereby readily informing the user as to the operational status of electrical stimulator apparatus 10. In one prototype of electrical stimulator apparatus 10 light 40 was configured as a green light while light 41 was configured as a red light when illuminated. Clearly, of course, if the battery is completely dead neither light 40 nor light 41 will illuminate.

As shown in FIG. 2, housing 12 is configured to be concealingly received within the confines of a hand 60 to thereby substantially conceal, if desired, the main body of electrical stimulation apparatus 10 while allowing electrodes 16 and 17 to protrude therefrom. This concealment is made possible by the relatively small size of electrical stimulation apparatus 10, that is, having a length overall of, say, 5 to 8 centimeters, a width of about 2 to 3 centimeters, and a thickness around one centimeter. Clearly, these dimensions are only approximate but they do emphasize the fact that electrical stimulation apparatus 10, particularly housing 12 portion thereof, is easily concealed, if desired, within the confines of hand 60. Another advantageous feature of electrical stimulation apparatus 10 is that it is provided with rounded corners externally to thereby render it less obtrusive when either handled by hand 60 or carried within a pocket or purse (not shown). Importantly, electrical stimulation apparatus 10 is specifically configured to be easily carried, easily concealed during use, and simple to operate to thereby specifically encourage the user to carry electrical stimulator apparatus 10 at all times and to use it whenever necessary regardless of the specific circumstances or surroundings. This is important since it enables the user to immediately apply electrical stimulation whenever the initial tactile sensation preceding a herpes lesion formation are felt by the user. Specifically, skin 62 is shown schematically as having a lesion 64 forming thereon. Electrodes 16 and 17 are being brought into contact with skin 62 to bracket lesion 64, the contact points for electrodes 16 and 17 on skin 62 being shown at 66 and 67, respectively. It should be noted that lesion 64 is shown herein as a visible lesion for purposes of illustration, it being the preferred intent of this invention to apply electrical stimulation to skin 62 with electrical stimulator apparatus 10 before lesion 64 becomes visible.

Figure 3:
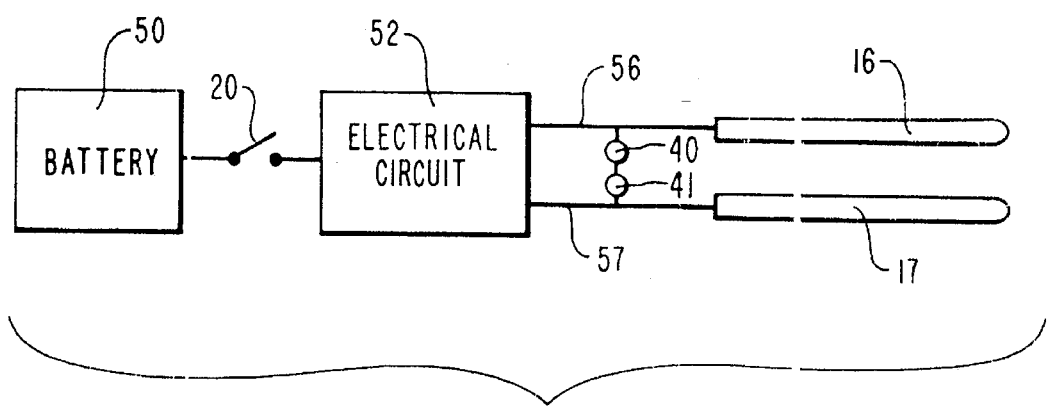
FIG. 3 is a schematic diagram of one embodiment of the electrical circuitry of my novel electrical stimulation apparatus.

Referring now to FIG. 3, one embodiment of the circuitry for electrical stimulator apparatus 10 is shown generally at 70 and includes a battery 50, an electrical circuit 52, and electrical leads 56 and 57 interconnecting electrical circuit 52 to electrodes 16 and 17 respectively. Switch 20 is interposed in a lead 54 between battery 50 and electrical circuit 52 and is manually operable to control the flow of electrical energy from battery 50 to electrical circuit 52 thence to electrodes 16 and 17. Lights 40 and 41 are connected across electrical leads 56 and 57. Light 40 provides a visual indication that electrical energy is being supplied to electrodes 16 and 17. Light 41 is a low battery indicator. The presence of lights 40 and 41 is important since the electrical energy supplied to electrodes 16 and 17 is too weak to be detected by the sensory perception of the user. Correspondingly, there would be no indication to the user that the battery was low if light 41 were not provided.

The Method

The novel method of this invention is practiced by the user (not shown) grasping electrical stimulator apparatus 10 in hand 60 and removing closure 14 to expose switch 20. The ends of electrodes 16 and 17 are touched to the surface of skin 62 to bracket lesion 64 as shown at 66 and 67, respectively. The user then depresses switch 20 to initiate the flow of electrical current from battery 50 through electrical circuit 52 to electrodes 16 and 17. Specifically, the closure of switch 20 sends electrical energy from battery 50 through lead 54 to the circuitry of electrical circuit 52 which produces the desired electrical impulse to be delivered through leads 56 and 57 to electrodes 16 and 17, respectively. In the simplified schematic of circuitry of electronic circuit 70 as shown in FIG. 3 light 40 is shown connected directly across leads 56 and 57. This configuration provides a direct indication to the user that electrical energy is being delivered to electrodes 16 and 17. In the event insufficient electrical energy is being supplied by battery 50, light 41 will be illuminated as a low-battery indicator.

Passage of the resultant electrical energy through lesion 64 results in an alteration of its cellular structure so as to promote healing of lesion 64. While the precise mechanism for the promotion of healing of lesion 64 using electrical stimulator apparatus 10 is not fully understood, I have been able to demonstrate significant improvements in the healing rates for lesion 64.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for applying an electrical stimulus comprising:

a housing;

a pair of electrodes extending from said housing, said pair of electrodes including a first electrode and a second electrode, each of said first electrode and said second electrode having an elongated body having a first end and a second end, said first end being configured with a smooth profile for contacting tissue, said second end including detent means for releasably engaging said elongated body to said housing;

a battery means in said housing for supplying electrical current to said electrodes; and switch means on said housing for controlling said electrical current to said electrodes;

wherein said housing includes a closure and an undercut section adjacent to said electrodes and to said switch means, said undercut section receiving said closure to enclose said electrodes and said switch means.

2. The apparatus defined in claim 1 wherein said housing includes clip means for releasably engaging said detent means of said elongated body in said housing, said clip means also providing electrical contact with said elongated body.

3. The apparatus defined in claim 1 wherein said housing includes a first indicator light, said first indicator light illuminating when said switch means is activated and said battery is providing a predetermined amount of electrical current to said electrodes.

4. The apparatus defined in claim 3 wherein said housing includes a second indicator light, said second indicator light illuminating when said switch means is activated and said battery is not providing adequate electrical current to said electrodes.

5. The apparatus defined in claim 1 wherein said undercut section includes a recess formed around said switch means.

6. The apparatus defined in claim 1 wherein said closure is removably mountable to said housing to provide a smooth external profile to said apparatus.

7. The apparatus defined in claim 1 wherein said housing includes a retainer for receiving a key chain to tether said housing.

8. An apparatus for the application of electrical stimulation to tissue comprising:

a housing, said housing having a smooth external profile between a first end and a second end and an undercut section adjacent said first end of said housing;

a switch recessed within said undercut section of said housing;

a pair of electrodes extending from said first end of said housing, said electrodes each being formed with a cylindrical profile having a first end and a second end with a rounded tip on said first end and a sharpened tip on said second end, said sharpened tip including a recessed detent adjacent said sharpened tip, said housing including a spring clip for releasably engaging said detent;

a closure for said housing, said closure being received in said undercut section thereby providing a continuation of said smooth external profile of said housing across said closure and enclosing said electrodes;

a battery in said housing; and an electrical circuit in said housing electrically coupled between said battery and said electrodes, said switch means controlling electrical energy from said battery to said electrodes and through said electrical circuit.

9. The apparatus defined in claim 8 wherein said electrodes are releasably mounted to said housing.

10. The apparatus defined in claim 8 wherein said housing includes a retainer for attaching said housing.

11. The apparatus defined in claim 8 wherein said housing includes a light means elctrically connected across said electrodes for providing a visual indication that electrical energy is being delivered to said electrodes.

12. The apparatus defined in claim 11 wherein said light means includes a low-battery indicator electrically coupled to said electrical circuit for providing a visual indication that said battery is not delivering sufficient electrical energy.

13. A method for applying electrical stimulation comprising:

selecting a housing capable of being held in a hand;

mounting an electrical circuit in said housing, said electrical circuit being operable for supplying an electrical stimulation;

coupling said electrical circuit to a battery thereby enabling said battery to provide electrical energy to said electrical circuit;

attaching a pair of electrodes to said electrical circuit, said pair of electrodes extending from said housing and thereby providing for delivery of said electrical stimulation;

controlling said electrical circuit with a switch;

contacting a surface to undergo electrical stimulation with said pair of electrodes; and applying electrical stimulation to the surface by operating said swinish thereby activating said electrical circuit and applying said electrical stimulation with said pair of electrodes;

wherein said selecting step includes shielding said electrodes against contamination by enclosing said pair of electrodes and said switch with a closure removably mounted to said housing.

14. The method defined in claim 13 wherein said applying step includes visually observing when electrical stimulation is being applied by connecting a light means to said electrical circuit said light means indicating that said switch has been activated and that electrical energy is being supplied to said pair of electrodes.

15. The method defined in claim 13 wherein said applying step includes assuring sufficient battery power for said electrical circuit by coupling a second light means to said electrical circuit for indicating a low battery condition of said battery.

* * * * *